Figure 1:
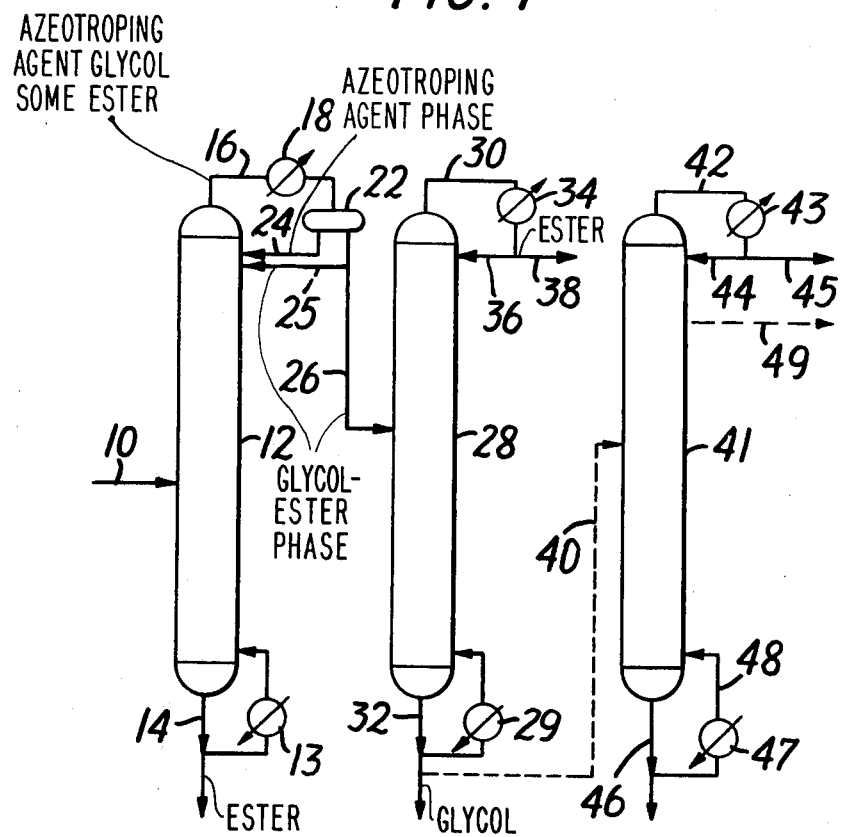

United States Patent [19]

Chueh

[11] 4,057,471
[45] Nov. 8, 1977

[54] RECOVERY OF ALKYLENE GLYCOLS

[75] Inventor: Chun Fei Chueh, Jamaica, N.Y.

[73] Assignee: Halcon International, Inc., New York, N.Y.

[21] Appl. No.: 612,825

[22] Filed: Sept. 12, 1975

[51] Int. Cl.² .............................................. B01D 3/36
[52] U.S. Cl. ........................................ 203/69; 203/98; 260/637 R
[58] Field of Search ....................... 203/98, 39, 50–70; 260/637 R

[56] References Cited

U.S. PATENT DOCUMENTS

| 3,437,566 | 4/1969 | Gasser et al. | 203/69 |
| 3,809,724 | 5/1974 | Golden | 260/637 R |

OTHER PUBLICATIONS

Weissberger, Technique of Organic Chemistry, vol. IV, Distillation, 1965, pp. 149–154, & 500–503.

Primary Examiner—Norman Yudkoff
Attorney, Agent, or Firm—William C. Long; David Dick; Riggs T. Stewart

[57] ABSTRACT

Ethylene glycol or 1,2-propylene glycol contained in mixtures with lower carboxylate esters of the glycol is recovered by azeotropic distillation of the mixtures with an azeotroping agent forming a minimum boiling azeotrope with the ethylene glycol or the 1,2-propylene glycol, the distillation being effected with reflux of azeotroping agent as well as controlled reflux of the glycol to the distillation zone.

11 Claims, 2 Drawing Figures

RECOVERY OF ALKYLENE GLYCOLS

This invention relates to the recovery of ethylene glycol or 1,2-propylene glycol from mixtures containing the glycol in admixture with lower carboxylate esters of the glycol, i.e., the ethylene or propylene glycol monocarboxylate and/or the ethylene or propylene glycol dicarboxylate. The invention is more particularly concerned with the recovery of the glycol from mixtures produced by the hydrolysis of lower carboxylate esters of the glycol.

Ethylene glycol and 1,2-propylene glycol (hereafter referred to as propylene glycol) are chemicals of acknowledged commercial importance. Ethylene glycol is used, for example, in the preparation of anti-freeze compositions and in the manufacture of polyester fibers. Ethylene glycol manufacturing processes of commercial interest have generally been based upon ethylene oxide as a raw material. Recently, however, processes hve been developed which make it possible to produce ethylene glycol and propylene glycol without the necessity for the intermedite manufacture of the oxide. These processes employ the liquid phase reaction of the olefin, a carboxylic acid and molecular oxygen in the presence of a catalyst to produce carboxylic acid esters of ethylene or propylene glycol. A process of this type is disclosed in Belgian Pat. No. 738,104. The glycol can be liberated by hydrolysis of the carboxylate esters produced in these processes. The conversion of the esters to the glycol is limited by equilibria and the recovery and separation of the glycol produced in the hydrolysis reaction from the unconverted carboxylate esters involves many difficulties because of the formation of glycol-carboxylate ester azeotropes.

It is an object of this invention to provide a process for the effective recovery of ethylene glycol or propylene glycol from mixtures of the glycol with lower caboxylate esters of the glycol.

It is an additional object of this invention to provide a process for the effective recovery of ethylene or propylene glycol produced by the hydrolysis of lower carboxylte esters of the glycol.

It is a further object of the invention to provide a process for the separation of ethylene glycol or propylene glycol from reaction mixtures produced by the hydrolysis of lower carboxylate esters of the glycol which can be integrated with the hydrolysis step itself.

Other objects of the invention will be apparent from the following description of the invention and of illustrative embodiments thereof.

The following description is presented with reference to ethylene glycol, it being understood that the description is equally and fully applicable to propylene glycol.

In accordance with the invention, ethylene glycol is separated from mixtures thereof with lower carboxylate esters of ethylene glycol, such as those produced by the hydrolysis of lower carboxylate esters of ethylene glycol, by distilling such mixtures in the presence of an azeotroping agent which is essentially water-immiscible, i.e., is immiscible or is only partially miscible in water, and which forms a minimum-boiling azeotrope with ethylene glycol and which preferably has a boiling point at atmospheric pressure of 135° to 220° C, most preferably 150° to 200° C. It has been found that when the ethylene glycol containing mixture is distilled in the presence of such azeotroping agents, the tendency of ethylene glycol to form azeotropes with the mono- and di-ethylene glycol carboxylates is no longer a hindrance to the separation of ethylene glycol from the mixture and ethylene glycol along with the added azeotroping agent can be readily removed by distillation from the mixture, and the ethylene glycol can then be easily recovered from the distillate. Indeed, the distillate, when condensed, separates into two phases, viz., a phase composed essentially of the azeotroping agent and a phase containing the ethylene glycol. The phase containing the azeotroping agent is readily separated, as by decantation, from the ethylene glycol-containing phase and is returned to the distillation column as reflux, preferably at the top of the column but suitably at a lower point in the upper portion of the column if desired. Azeotroping agent dissolved in the ethylene glycol phase removed from the column can be subsequently recovered, e.g., in a later distillation, and returned to the azeotropic distillation column, if desired. Consequently, the azeotroping agent is merely recirculated in the distillation system and the originally-supplied quantity of azeotroping agent is continually available for reuse except for the very small normally-encountered handling losses. At the same time, in accordance with the invention, a controlled quantity of the glycol, suitably in the form of the glycol-containing phase, is also returned to the distillation column as reflux. The reflux ratio of the glycol-containing phase is typically at least 0.3:1, preferably at least 0.5:1 and most preferably at least 1:1. From a practical standpoint, the reflux ratio of the glycol-containing phase is not generally above 8:1, although it can be higher if desired. Preferably, all of the phase containing the azeotroping agent is returned to the distillation column as reflux. It has been surprisingly discovered that when both the azeotroping agent and the product glycol are refluxed to the distillation zone in this manner there is a significant improvement in the purity of the glycol removed as distillate.

The most convenient way to supply glycol reflux to the azeotropic distillation column in accordance with the invention is, as previously indicated, to return part of the glycol-containing phase which is obtained upon condensation of the distillate. It will be apparent, however, that the glycol reflux may be obtained from a different source. For example, some of the glycol obtained in a distillation subsequent to the azeotropic distillation, e.g., in column 28 or in column 41 of the system shown in the drawing, may be used as reflux instead of directly using the glycol-containing phase. Alternatively, some of the glycol-containing phase may be used as reflux and be supplemented, for example, by glycol from column 28 or 41; or from some other source. In any case, the reflux ratio would be within the ranges previously described, i.e., the glycol or glycol-containing stream being fed as reflux will bear a relationship to the glycol-containing stream being withdrawn from the azeotropic distillation system within the above-indicated ranges. It will also be apparent that by adjustment of the temperature of the condensate more or less of the glycol in the distillate may remain dissolved in the phase containing the azeotropic distillation agent. In this case, the amount of reflux of the glycol-containing phase will be adjusted to refect the amount of glycol being returned to the azeotropic distillation column dissolved in the azeotropic agent phase. In an extreme situation, all of the glycol being returned as reflux may be contained in the azeotropic agent phase.

The azeotropic distillation of mixtures of ethylene glycol or propylene glycol with lower carboxylate esters of the glycol to separate the glycol from such esters has been proposed in Golden U.S. Pat. No. 3,809,724, the disclosure of which is incorporated herein by reference. While effective separation of the glycol is obtained by the process of that patent and the glycol contained in the distillate from the azeotropic distillation zone has a substantially lowered content of glycol esters, there is nevertheless a significant quantity of the glycol monoester which distills over with the glycol and requires the subjecting of the glycol-containing distillate phase to further distillation in order to remove this ester component, as shown in U.S. Pat. No. 3,809,724. In view of the quantity of molar monoester present relative to glycol, the subsequent fractional distillation requires a rather large distillation column in order to bring about the desired separation and there necessarily is a loss of glycol in this purification step. It has been discovered that the amount of glycol ester present in the overhead glycol phase can be unexpectedly material reduced by the glycol reflux process of this invention so that an overhead glycol phase can be obtained which contains much reduced quantities of monoester, with the result that the further distillation of the glycol phase to purify it can be carried out in a much smaller column and the loss of glycol in that purification operation is significantly reduced.

Typically, the glycol-containing phase from the azeotropic distillation will be substantially free from the glycol diesters contained in the feed to the azeotropic distillation but glycol monoesters will be present since, although undergoing substantial separation in the azeotropic distillation, they tend to pass in part into the overhead and this is particularly true of acetates and formates, especially the formates. In a typical case, the feed to the azeotropic distillation column contains ethylene glycol and ethylene glycol mono-esters in the ratio of about 0.1 to 1 mol of ethylene glycol to 1 mol of ester and the ethylene glycol-containing phase contains ethylene glycol in the ratio of 1.4 to 16 mols of ethylene glycol to 1 mol of monoester. The further fractional distillation, however, effectively removes these monoesters along with any azeotroping agent which may be present and makes possible the ready recovery as a bottoms product of substantially pure ethylene glycol. In general, the azeotropic distillation process of this invention is particularly applicable to ethylene glycol-ester mixtures containing 5 to 95 mol percent of ethylene glycol.

In the case of glycol monoacetates, a typical feed to the azeotropic distillation contains 0.5 to 2 mols of glycol to 1 mol of monoacetate and the ethylene glycol-containing phase contains 5 to 25 mols of glycol to 1 mol of monoacetate. Similarly, in the case of glycol monoformates, a typical feed to the azeotropic distillation contains 1.5 to 5 mols of glycol to 1 mol of glycol monoformate and the ethylene glycol-containing phase contains 3 to 10 mols of glycol to 1 mol of glycol monoformate. In a typical case, the process of the invention is effective to reduce the monoacetate content of the glycol-containing phase to below 10%, e.g., about 1 to 5 mol % and to reduce the monoformate content of the glycol-containing phase to about 10 to 20 mol %.

Suitably, the azeotroping agent has a boiling point within the aboveindicated 135° to 220° C range at atmospheric pressure, most advantageously within the specified preferred temperature range. Particularly suitable as azeotroping agent are the saturated hydrocarbons, both acyclic and cyclic, the aromatic hydrocarbons, which are for the most part, alkyl-substituted benzenes, and the halogenated hydrocarbons, especially halogenated aromatic hydrocarbons. Especially preferred azeotroping agents are the trimethylbenzenes, particularly 1,2,3-trimethylbenzene. Azeotroping agents also include ethers, ketones and alcohols. Table A below identifies examples of azeotroping agents of this character and indicates the boiling point of the azeotrope with ethylene glycol.

TABLE A

| Azeotroping Agent | Azeotrope b.p., °C 760 mm. Hg | Agent b.p., °C 760 mm. Hg |
| --- | --- | --- |
| Ethylbenzene | 133 | 136.2 |
| Cumene | 147 | 152.8 |
| Anisole | 150.5 | 153.9 |
| Bromobenzene | 150.2 | 156 |
| 1-Bromohexane | 150.5 | 156 |
| 1,2,3-Trichloropropane | 150.8 | 156.9 |
| Propylbenzene | 152 | 159 |
| o-Chlorotoluene | 152.5 | 159 |
| 2,7-Dimethyl Octane | 153 | 160 |
| p-Chlorotoluene | 155 | 162 |
| Mesitylene | 156 | 164.6 |
| 1,3-Dibromopropane | 160.2 | 167.3 |
| 2,6-Dimethyl-4-Heptanone | 164.2 | 168 |
| Pseudocumene | 158 | 169.5 |
| Phenetole | 161.5 | 172 |
| m-Dichlorobenzene | 166 | 172 |
| 2-Octanone | 168 | 172.9 |
| Benzylmethyl Ether | 159.8 | 174 |
| Decane | 161 | 174 |
| p-Dichlorobenzene | 163 | 174 |
| Hemimellitene | 163 | 176.1 |
| Heptyl Alcohol | 174.1 | 177 |
| p-Cymene | 163.2 | 177 |
| p-Methylanisole | 166.6 | 177 |
| Bis-(2-chloroethyl)Ether | 171 | 178 |
| o-Dichlorobenzene | 165.8 | 179 |
| n-Butyl Benzene | 166.2 | 183.1 |
| 1,2-Diethylbenzene | 168 | 183.4 |
| Benzyl ethyl Ether | 169 | 185 |
| Amyl Ether | 168.8 | 187.5 |
| Phenyl propyl Ether | 171 | 190.2 |
| p-Tert.-Butyl Toluene | 173 | 193 |
| Durene | 174 | 194 |
| n-Octyl Alcohol | 184 | 195.2 |
| Isodurene | 175 | 197 |
| Acetophenone | 186 | 202 |
| Prehnitene | 176 | 204 |
| Benzyl Alcohol | 193 | 205 |
| Tetralin | 178 | 207.2 |
| Dodecane | 179 | 214.5 |
| Benzyl Acetate | 186.5 | 214.9 |
| 1,3,5-Triethyl Benzene | 183 | 215.4 |

As indicated above, the separation process of the invention is applicable to the recovery of ethylene glycol from mixtures of this compound with ethylene glycol lower carboxylate esters produced in any manner, but it is so particular utility in the separation of ethylene glycol from such mixtures produced by the hydrolysis of mono- and/or di-carboxylate esters of ethylene glycol and the separation process can be readily integrated with the hydrolysis operation. The ethylene glycol-ester feed which is fed to the azeotropic distillation operation of this invention is a mixture of ethylene glycol with lower carboxylate monoesters and/or diesters of ethylene glycol, i.e., esters of ethylene glycol and an alkanoic acid having from 1 to 6 carbon atoms per molecule, such as formic acid, acetic acid, propionic acid, butyric acid, isobutyric acid, and the valeric and the caproic acids. Accordingly, the lower carboxylate monoesters of ethylene glycol include ethylene glycol monoformate, ethylene glycol monoacetate, ethylene glycol monopropionate, ethylene glycol monobutyrate, ethylene glycol monoisobutyrate, the ethylene glycol monovalerates and the ethylene glycol monocaproates, and the diesters include the corresponding diesters of the same alkanoic acids. Ethylene glycol admixed with the ethylene glycol monoformate, ethylene glycol monoacetate, monopropionate, monobutyrate and monoisobutyrate, the corresponding diesters and mixtures of such monoesters and such diesters, are typical feedstocks and the diacetate-monoacetate mixtures are particularly typical feedstocks. Of course, the ethylene glycol to be separated can also be present in mixtures of esters such as mixtures of ethylene glycol monoacetate and ethylene glycol monoformate, as well as mixtures with one or more diesters, including mixed diesters such as ethylene glycol acetate propionate. As used herein, therefore, the term "ethylene glycol-ester feed" is intended to include not only mixtures of ethylene glycol with the lower carboxylate ethylene glycol monoester alone or the ethylene glycol diester alone but also mixtures with monoester-diester mixtures or with mixed esters, as well as with mixtures of different ethylene glycol carboxylate esters. In general, mixtures containing the ethylene glycol may contain small amounts of by-products associated with the preparation of the glycol ester. Such by-products may normally include small quantities of water and acids, as well as catalyst residues and aldehydic by-products, e.g., acetaldehyde and formaldehyde.

The azeotropic distillation process of this invention is particularly applicable to ethylene glycol-ester mixtures containing 5 to 95 mol percent of ethylene glycol.

The distillation unit in which the azeotropic distillation of the invention is carried out can be any convenient fractional distillation unit, e.g., a plate column or a packed column, having a sufficient number of theoretical plates for the desired separation, generally from 15 to 50 theoretical plates. The temperature will, of course, vary with the particular azeotroping agent, since each agent forms a minimum-boiling binary azeotrope with ethylene glycol having a different boiling point but, in general, pot temperatures of 170° to 240° C are employed in the distillation. Similarly, pressures of from 400 mm.Hg to 50 psig are suitably employed. The azeotrope, when condensed, separates into a first phase, generally the upper phase, composed primarily of the azeotroping agent and into a second phase, generally the lower phase, composed primarily of ethylene glycol; this ethylene glycol phase may contain a small amount of ethylene glycol monocarboxylate ester which, when present in the system, will tend to distill with the azeotropic mixture to a greater or lesser extent depending on the azeotroping agent employed. The vapor condensate from the azeotropic distillate operation is therefore passed to a separator or decanter and the azeotroping agent-containing phase is returned as reflux to the distillation column. At the same time, in accordance with the preferred embodiment of the invention, a controlled quantity of the glycol-containing phase is also returned to the distillation column as reflux. It will be understood, however, that operation outside the above-mentioned temperature and pressure ranges is possible and, the specific choice of specific combinations of conditions is entirely within the scope of persons skilled in the art.

Ethylene glycol is recovered from the glycol-containing phase by distillation, extraction, or other appropriate means, although distillation is preferred. Suitably, the ethylene glycol-containing phase from the azeotropic condensate is subjected to further distillation to remove an overhead comprising any ethylene glycol monocarboxylate ester which may be present along with a relatively small amount of ethylene glycol, together with any azeotroping agent which may be present, and pure ethylene glycol is withdrawn as bottoms product. This distillation is carried out under appropriate distillation conditions, most suitably at temperatures of 120° to 210° C., and pressures of 50 mm. Hg to 7 psig. Any azeotropic agent present in the overhead product from this last-mentioned distillation step will generally phase separates and is advantageously recycled to the azeotropic distillation column. The glycol-ester phase can be recycled to an ester hydrolysis step, e.g., when the azeotropic distillation of this invention is integrated with the hydrolysis of glycol esters.

As previously mentioned, the ethylene glycol recovery process of this invention is particularly adapted to be integrated with the hydrolysis of ethylene glycol lower carboxylate esters, i.e., ethylene glycol lower carboxylate monoesters, diesters and mixtures of monoesters and diesters, i.e., it can follow the hydrolysis operation in order to recover the ethylene glycol which is produced. Thus, the ethylene glycol-ester feed to the azeotropic distillation can comprise the effluent from the hydrolysis of ethylene glycol carboxylate esters, suitably after removal of water and carboxylic acid, which effluent will contain not only the ethylene glycol monoester and generally the ethylene glycol diester but will also contain varying amounts of ethylene glycol. Thus, the reaction mixture from which the ethylene glycol is to be separated can be prepared by partially hydrolyzing mono- or di-carboxylate esters of ethylene glycol, or mixtures of said esters, by heating the ester or esters in the presence of water. Althrough the hydrolysis reaction will take place solely under the influence of heat, it may be preferred, in order to increase the rate of reaction, to effect hydrolysis in the presence of an acidic hydrolysis catalyst.

The feed to the hydrolysis operation can consist essentially of the monoester, or of the diester, or of mixtures of mono- or diesters in any proportion. The effluent from reactions which produce ethylene glycol monoester or ethylene glycol diester, or mixtures of the two, can be fed to the hydrolysis reaction. Typical reaction effluents of this nature are described, for example, in the above-mentioned Belgian Pat. No. 738,104 wherein the monoester is produced in the presence of substantial quantities of the diester, and in British Pat. No. 1,124,862, wherein the production of monoester substantially free from diester is disclosed. The hydrolysis step can be applied to glycol esters produced in any manner, whether by the process of the Belgian patent or the British patent or by various other processes. The hydrolysis reactions, regardless of the exact composition of the feed, continue until an equilibrium mixture comprising diester monoester, ethylene glycol, carboxylic acid and water is formed. Before feeding the hydrolysis reaction product to the azeotropic distillation, the water and carboxylic acid are preferably removed from the hydrolysis effluent, e.g., by distillation in any convenient manner, these two compounds being readily separated from the ethylene glycol and the lower carboxylate esters. In effecting the hydrolysis, the ethylene glycol lower carboxylate ester, or ester mixture, is suitably heated in the presence of water until at least some hydrolysis has occurred. Although the hydrolysis reaction will take place solely under the influence of heat, it may be preferred, in order to increase the rate of reaction, to effect hydrolysis in the presence of small amounts of an acidic hydrolysis catalyst such as a mineral acid, e.g., sulphuric acid and phosphoric acid, but most preferably a solid catalyst, e.g., in the form of an acidic ion exchange resin, is employed, as described in the previously-mentioned Golden U.S. Pat. No. 3,809,724. The hydrolysis step is thus suitably carried out by causing the glycol ester or ester mixture to react under the influence of heat (with or without a catalyst) to librate (i.e., hydrolyze) from 15 to 80 mol % of the acyl moieties, e.g., acetate moieties, as lower carboxylate acid, e.g., acetic acid, desirably using at least 0.25 mol of water, preferably 0.75 to 5 mols of water, per equivalent of acyl moiety present in the hydrolysis feed. In the course of the hydrolysis, ethylene glycol is liberated.

Hydrolysis reaction temperatures of at least about 50° C are generally used but, when catalysts are employed, temperatures as low as 25° C can be satisfactorily used. It is generally not desirable to employ hydrolysis reaction temperatures above about 250° C. Preferably, temperatures of about 50° to about 200° C are employed. Pressure is not critical as long as it is sufficient at the prevailing temperature to keep the reaction mixture in the liquid phase. Thus, pressures of as little as 50 mm. Hg can be employed as also can pressures of several thousand psia. Residence time of reactants and products within the hydrolysis zone is not critical. Thus, for example, residence times from as little as 1 minute up to and including several hours, e.g., 4 hours, or longer are entirely feasible.

Following the hydrolysis reaction, the hydrolyzate, which contains carboxylic acid, e.g., acetic acid, and water, in addition to the ethylene glycol, monoesters, and diesters, is, as mentioned, suitably passed into a distillation column wherein a major portion of the carboxylic acid and water is vaporized and removed as overhead for subsequent recovery. This separation can be carried out in any conventional distillation column, such as used for the azeotropic distillation. In general, it is desirable to separate at least 90% of the water and carboxylic acid present in the mixture before proceeding with the removal and recovery of the ethylene glycol by azeotropic distillation. Although the distillation step to separate water and carboxylic acid can be carried out over a wide range of conditions, it has been found preferable to operate at pot or preboiler temperatures of 170° to 240° C and at pressures of from 400 mm. Hg to 50 psig. It will be understood that the water and carboxylic acid can be removed in a single distillation operation or the distillation may be carried out in two distillation zones in series with the water and some of the carboxylic acid being removed in the first distillation zone and the remainder of the carboxylic acid to be removed being separated in the second distillation zone. The distillation can be carried out in conventional manner and the selection of specific conditions for treatment of specific feeds will be readily apparent to persons skilled in the art. The above-described hydrolysis and preliminary distillation are suitably carried out in the manner discussed and exemplified in Golden U.S. Pat. No. 3,809,724.

Figure 2:
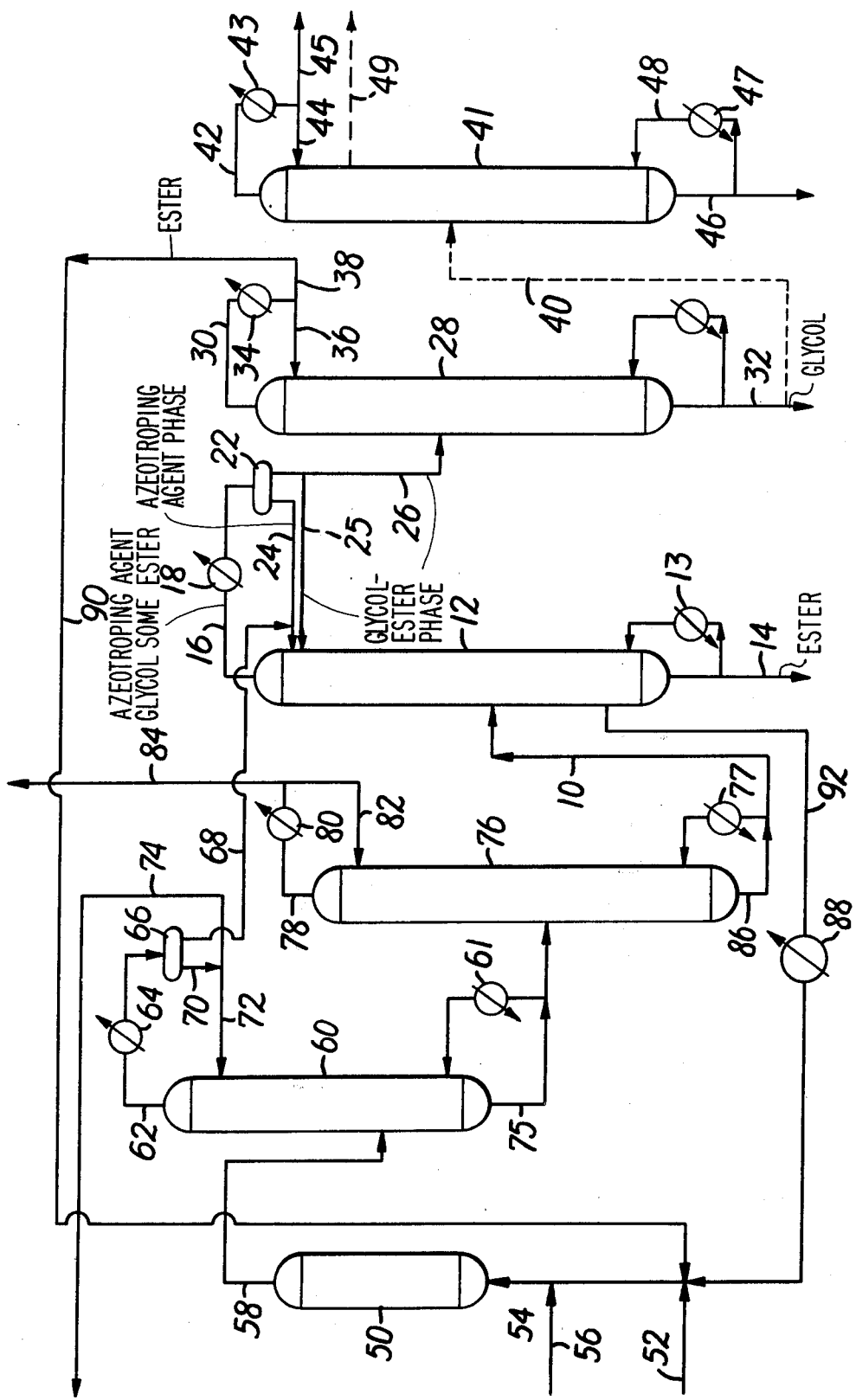

The invention will be moe fully understood by reference to the accompanying drawing, wherein:

FIG. 1 is a diagrammatic view of an ethylene glycol recovery system embodying the azeotropic distillation system of the invention, and FIG. 2 is a similar diagrammatic view of an overall system wherein the azeotropic distillation recovery system is integrated with an ethylene glycol ester hydrolysis.

Referring to the drawing, and more particularly to FIG. 1, an ester feed stream comprising an ethylene glycol ester mixture is fed through line 10 to azeotropic distillation zone 12 which, in the embodiment illustrated, is a distillation column suitably provided with heating means, e.g., a convenient reboiler 13 and with a bottoms withdrawal line 14 and an overhead vapor line 16, the latter being connected to a condenser 18. The ethylene glycol is removed through line 16 in the form of vapor along with the azeotroping agent, and glycol ester is withdrawn through line 14. The overhead vapor from column 12 leaves through line 16 and is condensed in condenser 18, flows to a phase separator 22, and the condensed azeotroping agent is returned to column 12 through line 24 as reflux, whereas the ethylene glycol phase is withdrawn through line 26 and is introduced into a refining column 28, also provided with a heating means, suitably in the form of a reboiler 29. A portion of the ethylene glycol phase is suitably returned through line 25 to zone 12 as reflux as above described in accordance with the process of the present invention. In column 28, ethylene glycol ester and azeotroping agent contained in the ethylene glycol phase withdrawn from phase separator 22 is removed as vapor through line 30, and ethylene glycol in substantially purified form is withdrawn as bottoms through line 32. The vapors in line 30 are condensed in condenser 34 and a portion is returned as reflux to column 28 through line 36 and the remainder is withdrawn through line 38. Portions of the material in line 38 may, if desired, be combined with the feed to column 12, and make-up azeotroping agent, as required, may be suitably added through line 10 or added to line 24. Preferably, the purified ethylene glycol withdrawn through line 32 is given a final distilltion to insure against the presence in the product of higher boiling materials such as diethylene glycol and the like, which may tend to form in small amounts. Thus, if this further distillation is desired, the ethylene glycol from line 32 is passed through line 40 into distillation column 41 which is operated at temperatures of 120° C to 190° C and pressures of 40 mm to 600 mm to remove purified glycol through line 42 leading to condenser 43, the condensate from which is partially returned to column 41 as reflux through line 44, and the remainder is withdrawn through line 45. The heavier components separated by the distillation are removed through line 46. The reboiler 47 in line 48 provides the necessary heat to maintain the distillation.

If desired, the upper few plates, e.g., 2-3 theoretical plates, of column 41 are used as a conventional "pasteurization" section, i.e., the product glycol is removed as a side stream through line 49, and the entire distillate passing into line 42 and condenser 43 is returned as reflux through line 44 except for the withdrawal of a small portion through line 45 containing lower-boiling components which may be present.

Referring now to FIG. 2, wherein the azeotropic distillation system just described is integrated with the hydrolysis of lower carboxylate esters of ethylene glycol to provide the feed to azeotropic distillation column 12, a hydrolysis ester feed stream enters a hydrolysis zone 50 through line 52 and line 54 and water for the hydrolysis enters through line 56 and is combined with the hydrolysis ester feed in line 54 before entering zone 50. Zone 50 is suitably filled with a bed of solid hydrolysis catalyst, e.g., a bed of acidic ion exchange resin and the combined water and ester feed stream flows upwardly through the bed and the hydrolyzed reaction product is removed through line 58. The product stream in line 58 is introduced into a water separation column 60, provided with a reboiler 61 or other heating means. In column 60, water is vaporized and, along with a small amount of carboxylic acid, is withdrawn through line 62 and condensed in condenser 64. Since, in the embodiment illustrated in FIG. 2, the condensate from condenser 64 will contain some azeotroping agent, as will be explained below, the condensate passes to a phase separator 66 wherein the water and carboxylic acid form one phase and the azeotroping agent forms a second phase, the latter being withdrawn from separator 66 through line 68. The aqueous phase is withdrawn through line 70, with part of it being returned to column 60 through line 72 as reflux and the remainder being recycled to reactor 50 through line 74 which empties into water supply 56. The portion of the hydrolysis product stream supplied to column 60 which is not vaporized and withdrawn through line 62 and which comprises ethylene glycol, carboxylic acid and lower carboxylate esters of ethylene glycol is withdrawn through line 75 and fed to a distillation column 76, also provided with appropriate heating means, e.g., a reboiler 77. In distillation column 76, the carboxylic acid is vaporized and carboxylic acid vapors are withdrawn through line 78 and condensed in condenser 80 with some of the condensate being returned to column 76 as reflux through line 82 and the remainder being withdrawn from the system through line 84. The carboxylic acid stream will also contain any water which was not separated in column 60. The essentially water- and carboxylic acid-free ethylene glycol-lower carboxylate ester mixture is withdrawn from distillation zone 76 through line 86 and is supplied to line 10 to provide the ester feed to azeotropic distillation zone 12, as described above in connection with the discussion of FIG. 1. To complete the integration of the azeotropic distillation system with the hydrolysis system, a line 90 connects with line 38 to conduct the withdrawn condensate containing azeotroping agent from column 28 to the feed to hydrolysis zone 50 and side stream from column 12 comprising vapors of lower carboxylate esters of ethylene glycol is withdrawn through line 92 and also combined with the feed of the hydrolysis zone, after being condensed by condenser 88.

The following examples of specific application will serve to give a fuller understanding of the invention but it will be understood that these examples are illustrative only and are not intended as limiting the invention.

EXAMPLE 1

Using a distillation column of 30 theoretical plates and 2 inches diameter, there was fed continuously to the 12th plate of the column at the rate of 2200 g/hr an impure ethylene glycol composed of 34.6 mol % of ethylene glycol (EG), 42.2 mol % of ethylene glycol monoacetate (EGMA), 12.8 mol % of ethylene glycol diacetate (EGDA), 7.9 mol % ethylene glycol monoformate (EGMF) and 2.5 mol % ethylene glycol acetate formate (EGAF). This column is operated under a pressure of 30 psig with a bottoms or reboiler temperature of 230° C, and an overhead temperature of 205° C. The feed mixture is azeotropically distilled in the column under the conditions indicated in the presence of diethylbenzene (commercial mixed isomer fraction, b.p. 181°-184° C.) as the azeotropic distillation solvent. The distillation is operated with total reflux of the azeotropic solvent and with partial reflux of the ethylene glycol phase. Thus, the overhead vapors are condensed and the condensed two-phase liquid is separated, i.e., the heavier liquid comprising ethylene glycol and monoester is drawn off and the lighter liquid comprising the diethylbenzene (DEB) is decanted through the overflow line and is pumped to the top tray of the column at a fixed flow rate along with make-up DEB to provide a total reflux of the azeotroping agent phase. A portion of the ethylene glycol-containing phase is also returned to the top tray to provide various reflux ratios, viz., 1:1, 2:1, and 3:1.

During steady state operation 220 g. per hour of the feed mixture is continuously introduced at the feed point and DEB is introduced on the top plate to provide a mol ratio of DEB to total vapor at the top of the column of about 55%. Under these conditions the amount of DEB in the bottoms is about 0.1 to 1 mol%. The DEB supplied is the reflux of the lighter liquid from the decantation to which make-up DEB is added to compensate for that passing into the withdrawn overhead phase and into the bottoms. The composition of the product ethylene glycol recovered from the distillate at the several glycol reflux ratios is shown below, the molar ratio of EG to EGMA, EG to EGMF, and EG to total ester being indicated.

| Glycol reflux ratio | EG EGMA | EG EGMF | EG Total Ester |
|---|---|---|---|
| 1:1 | 7.6 | 4.6 | 2.9 |
| 2:1 | 23.1 | 5.9 | 4.7 |
| 3:1 | 74.0 | 7.2 | 6.5 |

In this distillation, 95% of the ethylene glycol fed is recovered in the distillate.

EXAMPLE 2

Example 1 is repeated in the manner described at 30 psig, except that 1,2,3-trimethylbenzene is used as the azeotropic distillation solvent, the reflux ratios of the ethylene glycol-containing phase are 1:1, 1.8:1, and 2.6:1, the bottoms or reboiler temperature is 230° C and the overhead temperature is 205° C. The composition of the product ethylene glycol recovered from the distillate at the several reflux ratios is shown below:

| Glycol reflux ratio | EG EGMA | EG EGMF | EG Total Ester |
|---|---|---|---|
| 1:1 | 6.6 | 5.8 | 3.1 |
| 1.8:1 | 13.5 | 7.3 | 4.8 |
| 2.6:1 | 21.3 | 8.6 | 5.9 |

EXAMPLE 3

Example 1 is again repeated with the diethylbenzene azeotropic distillation solvent of Example 1, but the distillation is carried out at 50 psig. In this case, the bottoms or reboiler temperature is 245° C and the overhead temperature is 220° C. The composition of the product ethylene glycol recovered from the distillate at the several reflux ratios is shown below:

| Glycol reflux ratio | EG EGMA | EG EGMF | EG Total Ester |
|---|---|---|---|
| 1:1 | 14 | 5.6 | 4.0 |
| 2:1 | 48 | 6.6 | 5.8 |

-continued

| Glycol reflux ratio | EG EGMA | EG EGMF | EG Total Ester |
|---|---|---|---|
| 3:1 | 167 | 7.9 | 7.5 |

When this example is repeated without reflux of the ethylene glycol-containing phase, i.e., only the total reflux of the azeotropic agent phase, the molar ratio of the ethylene glycol to total ester is 2, the molar ratio of ethylene glycol to ethylene glycol monoformate is 2.8, and the molar ratio of ethylene glycol to ethylene glycol monoacetate is 10.

Substantially pure ethylene glycol is readily obtained by fractional distillation of the ethylene glycol-containing product phase produced in the above-described azeotropic distillations. To effect this fractional distillation, the ethylene glycol-containing phase is continuously introduced into a fractional distillation column of the type used for the azeotropic distillation with 18 theoretical plates above the feed point and 22 theoretical plates below the feed point. This column is operated at a reduced pressure of about 150 mm.Hg with a bottoms of reboiler temperature of about 170° C and an overhead temperature of about 125° C, employing a reflux ratio of 2.3:1. More than 96% of the ethylene glycol in the feed to this distillation is recovered as the bottoms product and is in substantially purified form.

In order to increase the purity of the ethylene glycol even further, the overhead from the just-described distillation is continuously supplied to a fractional distillation column of the same type having 25 theoretical plates below the feed point and 15 theoretical plates above the feed point. This column (41) is operated at a reduced pressure of about 150 mm.Hg with an overhead temperature of 170° C, using a reflux ratio of 2.1:1, i.e., ratio of reflux via line 44 to glycol withdrawal via line 49. In this distillation, 98% of the feed is withdrawn as purified ethylene glycol (line 49), 1% is withdrawn as bottoms and 1% is withdrawn as a light overhead fraction.

As previously mentioned, while the invention has been primarily described and illustrated with reference to the recovery of ethylene glycol, similar results are obtained when the etylene glycol is replaced by propylene glycol. Thus, in the case of the azeotropic distillation, use is made of azeotroping agents of the character indicated which form minimum-boiling azeotropes with propylene glycol, which azeotropes generally have a slightly lower boiling point than the corresponding azeotropes of the azeotroping agents which ethylene glycol. Thus, with propylene glycol o-xylene forms an azeotrope boiling at 136° C, 2-octanone forms an azeotrope boiling at 169° C, 1,2,3-trimethylbenzene forms an azeotrope boiling at 162° C, tert.-butyl benzene forms an azeotrope boiling at 155° C, and p-tert.-butyl toluene forms an azeotrope boiling at 169° C.

It will be understood, therefore, that all matter contained in the foregoing description and illustrated in the drawing is to be interpreted as illustrative only and not as limitative of the invention and various changes and modifications which will be apparent to those skilled in the art may be made without departing from the scope of the invention as defined in the appended claims.

I claim:

1. A process for recovering ethylene glycol or propylene glycol from a mixture comprising propylene glycol or ethylene glycol in admixture with at least one of a mono-lower carboxylate ester and a di-lower carboxylate ester of said propylene glycol or ethylene glycol which comprises the steps of:
    a. subjecting said mixture to distillation in a distillation zone in the presence of an azeotroping agent effective to form a minimum-boiling azeotrope with said glycol, said azeotroping agent being essentially water and glycol immiscible and having a boiling point at atmospheric pressure of above 135° to about 220° C, whereby an overhead product and a bottoms product are produced, said overhead product comprising said azeotroping agent and said glycol and said bottoms product comprising said ester substantially reduced in glycol content;
    b. separating said overhead product into a first phase comprising said azeotroping agent and a second phase comprising said glycol;
    c. returning said first phase to said distillation zone as reflux;
    d. supplying a portion of the glycol as reflux to said distillation zone; and
    e. withdrawing the remainder of the glycol from said second phase as glycol product, wherein the ratio of the glycol supplied to the glycol withdrawn is at least 0.3:1.

2. A process as defined in claim 1, wherein the ratio of glycol supplied as reflux to the glycol-containing stream withdrawn from the azeotropic distillation system is at most 8:1.

3. A process as defined in claim 1, wherein the ratio of glycol supplied as reflux to the glycol-containing stream withdrawn from the azeotropic distillation system is at least 1.1.

4. A process as defined in claim 1, wherein said azeotroping agent is an aromatic compound.

5. A process as defined in claim 1, wherein said azeotroping agent is an aromatic hydrocarbon.

6. A process as defined in claim 1, wherein said azeotroping agent is a methyl-substituted benzene.

7. A process as defined in claim 1, wherein said azeotroping agent is 1,2,3-trimethylbenzene.

8. A process as defined in claim 1, wherein said azeotroping agent is a trimethylbenzene.

9. A process as defined in claim 1, wherein the glycol is ethylene glycol.

10. A process as defined in claim 2, wherein the glycol is ethylene glycol.

11. A process as defined in claim 5, wherein the glycol is ethylene glycol.

* * * * *